United States Patent
Casaña Giner et al.

(10) Patent No.: US 8,648,013 B2
(45) Date of Patent: Feb. 11, 2014

(54) OIL SUSPENSIONS OF SULPHONYLUREAS AND AGROCHEMICAL COMBINATIONS

(76) Inventors: Victor Casaña Giner, Ebenfurth (AT); Miguel Gimeno Sierra, Ebenfurth (AT); Barbara Gimeno Sierra, Ebenfurth (AT)

( * ) Notice: Subject to any disclaimer, the term of this patent is extended or adjusted under 35 U.S.C. 154(b) by 696 days.

(21) Appl. No.: 12/452,168

(22) PCT Filed: Jun. 18, 2008

(86) PCT No.: PCT/EP2008/004901
§ 371 (c)(1),
(2), (4) Date: Dec. 17, 2009

(87) PCT Pub. No.: WO2008/155108
PCT Pub. Date: Dec. 24, 2008

(65) Prior Publication Data
US 2010/0130364 A1     May 27, 2010

(30) Foreign Application Priority Data
Jun. 19, 2007   (ES) .................................. 200701796

(51) Int. Cl.
*A01N 43/60* (2006.01)
*A01N 47/36* (2006.01)

(52) U.S. Cl.
USPC ........... 504/136; 504/212; 504/213; 504/214; 504/215

(58) Field of Classification Search
None
See application file for complete search history.

(56) References Cited

U.S. PATENT DOCUMENTS 8,129,312 B2 *   3/2012   Berghaus et al. ........... 504/116.1
2008/0176746 A1 *   7/2008   Grohs et al. .................. 504/211

* cited by examiner

*Primary Examiner* — Alton Pryor
(74) *Attorney, Agent, or Firm* — Vedder Price PC

(57) ABSTRACT

An agrochemical formulation in the form of an oil suspension characterized in that it contains as essential elements of the formulation (percentages by weight related to the total weight of the formulation) at least; a herbicide of the sulphonylurea type at a concentration of 0.5-50%, preferably 2-30%, a paraffin mineral oil at a concentration of 10-75%, preferably without the existence of any other type of mineral or vegetable oil in the formulation and the concentration of mineral oil being 40-60%, an organomodified silane compound at a concentration of 5-40%, preferably 10-25%, with the existence of other coformulants until reaching 100% by weight of the formulation.

51 Claims, 1 Drawing Sheet

OIL SUSPENSIONS OF SULPHONYLUREAS AND AGROCHEMICAL COMBINATIONS

The present invention relates to oil suspensions of sulphonylureas (optionally combined with one another and/or with other active agrochemical ingredients) with very improved properties regarding stability (specifically the prevention of phase separation in the formulation itself and the stability of its emulsion in water by the farmer before application) based on the use of certain oils, dispersants and combinations of other coformulants.

BACKGROUND OF THE INVENTION

The present invention addresses the problem of formulating sulphonylureas for agrochemical use, alone or combined, such that both the packaged formulation, the emulsion made by the farmer and the active ingredient(s) (Als) are stable and maintain a suitable biological activity.

Mixtures of sulphonylureas with other active ingredients for broad-spectrum formulations, non-exclusively including herbicides, fungicides, insecticides and plant hormones are also contemplated.

The solution proposed in this invention is the formulation of said sulphonylureas (SU) (optionally with other Als) with certain coformulants (formulation ingredients other than the Al) in certain proportions, the combination of the base oil (solvent) with a derivative of organic silane of the commercial type Break Thru® (trisiloxane polyethers) being essential.

There are several problems associated with oil formulations of herbicides, the detection and characterization of which has been an essential part of the research carried out in order to overcome them, and which is therefore considered as part of the inventive step of this patent.

Among the problems found we can highlight:
i) During and after the grinding process, the sulphonylurea crystals tend to aggregate
ii) The use of oils in which sulphonylurea solubility is "relatively high" creates problems regarding biological activity, since part of the Al is in crystal form when applied; and part is dissolved in the base oil, specifically in those oils with low boiling points universal solubilising agents (for example, cyclohexanone).
iii) The stability of oil suspensions in the state of the art can be improved upon-since the usual viscosity modifiers in agrochemical formulations do not have the desired effect
iv) Biological activity is very related (especially with sulphonylureas) with the formulation's wetting ability
v) Al stability is very dependent on the medium (oil and coformulants)
vi) product homogeneity tends to be very low, with short-term phase separation Sulphonylureas are highly active herbicides with low toxicity.

It is understood that throughout this patent, the term sulphonylureas also includes the so-called sulphonamides. These two terms are occasionally used interchangeably or even confused: we would like to note that we always refer to both types with the term "sulphonylureas".

Non-restrictive examples of sulphonylureas object of the invention, are: amidosulfuron, azimsulfuron, bensulforon, chlorimuron, chlorsulfuron, cinosulfuron, cyclosulfamuron, ethametsulfuron, ethoxysulfuron, flazasulfuron, flupyrsulfuron, foramulfuron, halosulfuron, imazosulfuron, iodosulfuron, mesosulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, triflox-ysulfuron, triflusulfuron, tritosulfuron; as well as active herbicide derivatives (such as methyl, ethyl or alkyl ethers or esters) and salts thereof.

They are easily degradable, especially in aqueous mediums.

It is known that SUs can be formulated in oil medium in order to improve their stability.

Since it is a very important requirement of the agrochemical sector, there are numerous patents and articles relating to the same problem indicated in this invention, but they solve it by other means.

Some documents demonstrate that their formulation as oil suspensions improves SU stability, particularly when used in combination with urea. However, the stability of said formulations is far from optimal.

Our formulations, even without urea, show adequate stability. None of the tests performed with different products in the market have provided any formulation as stable as those proposed (e.g. Examples 1, A and B) since, despite the fact that adequate product stability and homogeneity can be obtained in laboratory conditions and with skilled handling, it is true that the products mentioned must be handled, amongst others, by farmers in their own facilities, and real usage conditions may therefore be very different from the conditions in which the laboratory tests were performed, causing a great reduction in product stability/homogeneity, and therefore a great reduction in product qualities: this relates essentially to the need of strong stirring and the necessary industrial application of the formulation (i.e. coformulant availability at the industrial level, their price realistically allowing industrial use).

Take as an example the photograph in FIG. 1, that shows a sample of the leading formulation of sulphonylurea nicosulfuron that in the market Motivell® (BASF), where there is an evident separation of the phases when left to settle for some days (15 days at room temperature and 8 at 54° C.).

Errors and omissions excepted, neither the applicant or the inventors know any commercially viable product that offers a stability such as the one proposed, neither, in fact, have they found anything at the commercial level or published in scientific articles or registered with stability characteristics such as those obtained by the product object of the present invention.

Some patents that describe-different solutions toe the aforementioned problem are:

WO2007/042152 (Vermeer et al., Bayer), wherein an SU is combined with pyrethroids, with the use of cyclohexanone (which is very inflammable and is not used in this invention).

DE10258216 (anonymous, Bayer), wherein a sulphosuccinate is necessarily used (we do not use sulphosuccinates in our invention).

US2006/0276337 (Sterne et al, Bayer) where it is shown in [0415] that the preferred embodiment required the use of a sulphosuccinate, as demonstrated in the examples and deduced from the description (we do not use sulphosuccinates in our invention).

WO2007/028517 (Bailo-Schleier-Macher et al., Bayer) where an oil suspension is used to fight against the eggs and nymphs of the white fly, being applicable only in neonicotinoids (not sulphonylureas)

WO2007/042138 (Schnable et al., Bayer) where polycation salts of certain solubility in water are used (not used in our invention)

EP554015 (Kanbayashi et al., ISK), where the use of sulphonylureas in oil suspensions is protected when combining an emulsifier, an oil and urea.

There are other patents dealing essentially with the type of oil used in the suspension, but none of them shows the preferred use of a paraffin oil with an organomodified silane derivative. For a better embodiment, we recommend the preferred use only of paraffin oils—or at least mixtures containing at least 10% of these—, since these paraffin oils in combination with the organomodified silane derivatives show greater stability than the rest when used according to our invention.

DESCRIPTION OF THE INVENTION

The invention propose refers essentially to the use of organic derivatives of silane (or siloxane), such as trisiloxane polyethers represented by several types of Break-Thru® compounds (e.g. those with CAS No. [67674-67-3], [134180-76-0], [27306-78-1]) in oil suspensions of sulphonylureas. The preferred concentrations with 5-40% or even better with 10-25%.

The amount of Al (alone or combined Als) must not be less than a minimum amount for herbicide efficacy (estimated at 0.5%) and not more than 50% in order to avoid problems of formulation stability, although logic dictates that we should tend as much as possible not to approach the upper limit, since the handling of these formulations is difficult due to their great viscosity and density, it being preferable not to use more than 30% in Al or a mixture of Als in suspended solid form.

The presence of a paraffin mineral oil is essential for our invention, at an estimated minimum of 10%.

The paraffin oil may be mixed with other mineral oils such as those mentioned above (e.g. naphtha) or with vegetable oils, although the use of only paraffin oil is preferred, in a concentration of not more than 75%, in order to include in the formulation the necessary coformulants to aid emulsification, crystal dispersion, modification of viscosity, etc. It is very convenient that no coformulants negatively affect the degradation of the sulphonylureas in the formulation. This is easily verified by performing the formulation at a certain concentration, leaving it in an oven at 35° C. for two weeks and verifying how much sulphonylurea has degraded. A value above 10% is completely unacceptable.

The most adequate concentrations of oil base are 40-60%, in order to make adequate room for the coformulants and Als.

Sulphonylureas (or sulphonamides) may be used in our formulations alone or combined with other sulphonylureas. One or several sulphonylureas can be used at the same time, and they can also be mixed with other agrochemical agents in the general sense (such as insecticides, other herbicides, fungicides, plant hormones, etc.), the latter alone or in combination and also dispersed in the oil phase or dissolved (totally or partially). The invention contemplates the case that the sulphonylureas are partially dissolved in the oil or even totally dissolved in the case of a second sulphonylurea combined with another that is in suspension.

It is possible, and occasionally convenient, that the Als that are not sulphonylureas are soluble (or partially soluble) in the oil phase, in which case we can have superemulsions.

We can also have ZC formulations (suspension of capsules+suspension concentrate), by means of the combination of microcapsule formulations.

The preferred combinations are of different herbicides with different modes of action, herbicide/insecticide, herbicide/fungicide.

The following combinations are especially preferred:

At least two sulphonylureas, preferably: metsulfuron with tribenuron, metsulfuron with thifensulfuron, nicosulfuron with rimsulfuron;

Any sulphonylurea with one of the following agrochemicals: fluoroxypyr, diflufenican, lactofen, mesotrione, sulcotrione, flurochloridone, metazachlor, clomazone (or a mixture of clomazone with metazachlor), pyrethroids (preferably alpha-cypermethrin, lambda-cyhalothrin, permethrin, resmethrin, allethrin), triazole fungicides (preferably tebuconazole, propiconazole, triadimenol), glyphosate (in salt form or more preferably as an acid); gluphosinate (in salt form or more preferably as an acid)

Mixtures of sulphonylureas according to 3 a. combined with agrochemicals according to 3 b.

It is perfectly possible to perform these combinations by grinding the insoluble Als in the oil phase at the same time as grinding the sulphonylurea(s), or solubilising said Als in the oil phase, if applicable.

BRIEF DESCRIPTION OF THE DRAWINGS

FIG. 1 shows a sample of Motivell® (BASF), the leading sulphonylurea nicosulfuron formulation in the market, which shows evident separation of phases when left to rest for a few days versus a sample of the formulation proposed by the applicant and object of the present invention, which maintained in the same conditions as the reference sample, shows optimal product homogeneity.

DESCRIPTION OF A PREFERRED EMBODIMENT OF THE INVENTION

The state of the art shows that oil suspensions of sulphonylureas are performed preferably in vegetable oils (e.g., coconut oil, sunflower oil) or in aromatic mineral oils (of the Solvesso®, light or heavy naphtha type).

Since commercial products with said oil composition do not result in adequate stability, the inventors have tried another type of oil: Isopar® and Marcol®, that is, paraffin oil.

The amount of oil to be used will depend on the active ingredient content—it is understood that the Al can be one or a combination of different sulphonylureas or even combinations of sulphonylureas with other Als, preferably with herbicidal action, wither an insecticide or fungicide or mixtures thereof, the use of Als with herbicidal activity being preferred.

Since it is more difficult to formulate a composition with a high Al concentration, the examples refer to this situation, since applying the invention to lower concentrations can be achieved simply by proportionally substituting the rest of coformulants for the difference in the amount of Al used with respect to the examples.

The oil phase must be formed by a paraffin oil in an amount of 40-60% (we always refer to % by weight/weight related to the total weight of the formulation).

For example, for an oil suspension with a 4% Al content (or total IA content), a suitable percentage of oil is approximately 43-67%, for about 20% of Al(s) a suitable oil content is 38-63%.

The commercial products corresponding to this oil are representatively designated by those of Exxon, that is, any of the Isopar® brand (comprising several paraffin petroleum fractions with different boiling points).

Both Isopar® M, and "V" or "L" or "K" provide good results, Isopar® M being extraordinarily adequate, as well as those with greater boiling points commercialised with the brand Marcol®.

The invention proposed works with other oils, both vegetable and mineral, as long as there is 10% of paraffin oil.

The properties of product and formulation and emulsion stability (not expected according to the state of the art for a formulation lacking sulphosuccinates) together with acceptable biological activity as well as the ease of the milling step is not achieved with the (combined) use of other non-paraffin oils, but still solves partial problems mentioned in this invention.

That is, the best embodiment of the invention is with paraffin oils; but a person skilled in the art may still achieve better formulations than those of the state of the art with non-paraffin oils and without mixing them with paraffin oils, but we insist, far from the extraordinary properties gained with the use of paraffin oils claimed herein.

However, we have not achieved formulations with acceptable stability without the use of organosilane derivatives of the Break-Thru® type (mainly trisiloxane polyethers with or without adjuvants) using this trade name since for a person skilled in the art it is clear what derivatives we refer to by naming a commercial product that representative of them all (much clearer for a person skilled in the art than a confusing name that may lead to not finding the product to be used in catalogues).

Vegetable oils that may be used are the usual ones in agriculture (castor oil, sunflower oil, coconut oil, corn, rape oil, etc), and mineral oils that can be used are all those offered by Exxon® for use in agriculture, particularly naphtha oils ((Solvesso® 100, 150, 200, etc—ND ("naphthalene depleted") or not) and pentanes, heptanes, etc.

It is understood that the catalogue of Exxon® products for application in agriculture on the date this invention is filed is incorporated to the present invention by reference.

It is also particularly surprising that mixtures in which paraffin oil is present in at least 20% (with respect to total solvent oil) with other oils (particularly of the Solvesso® type or vegetable oils—and mixtures thereof) also show stability above that of oil suspensions in the state of the art.

A compound we have observed as very interesting in preventing phase separation in the formulation and the emulsion are organomodified siloxanes, of the commercial type Break-Thru® (e.g. S 240, S 278).

It is especially surprising that these compounds are not described as dispersing or emulsifying agents (which is the function they perform in our invention before being applied in the field), but as wetting agents (that is, so that the drops of water extend over the leaves and fruits- or insects-treated). The recommendations of the manufacturer of these organomodified silanes prevents a person skilled in the art from thinking of using them to produce a formulation with improved stability properties (no oil separation), but exactly the opposite: a person skilled in the art would avoid using it for any purpose other than increasing the wetting effect.

Preferred silanes do not have to be restricted exclusively to the trisiloxane ether type: A person skilled in the art knows that modifications without excessively affecting said structure are very probably also suitable for use according to the present invention. This principle of chemical equivalents is applicable to the other coformulants.

A minimum content in silanes (siloxanes) according to our invention is of 5%, and it is recommended that it is present at 5-40%, preferably at 10-25%.

With the use of organomodified silanes we do not only achieve the main result sought by this invention (formulation stability) but also other important problems such as biological activity and Al stability.

We can understand that biological activity is improved due to the large amount of an agent that reduces the surface tension of water, however, why organomodified silanes prove to be products in which the stability of sulphonylureas is higher is a matter that we can only think to be due to the high hydrophobic environment they produce, because for some unknown reason they prevent sulphonylurea hydrolysis by means of some chemical process.

We have found that formulations with organomodified silanes exhibit similar stability to that obtained with known stabilisers such as urea. However, nothing prevents the combination of products of the Break-Thru® chemical type with urea in order to simultaneously obtain an unexpected double effect an increase in suspension and emulsion stability; and also in Al by double effect. (It is understood throughout this document that Al may refer to mixtures of different active ingredients, nevertheless it is understood that the improvement in chemical stability of the Al refers exclusively to sulphonylurea(s), which is precisely the labile type of Al).

Another compound that facilitates product stability is a viscosity modifier of the bentonite type.

Although in principle any viscosity modifier may be used, specifically all chemical equivalents of bentonite (bentone) [that is, clays, sepiolites, attapulgites, zeolites, talcs, silicates, aluminium silicates, etc. and mixtures thereof], we have observed that those with the chemical structure of the product "Bentone®" (and its different versions) are the ones that work best (effectively increasing viscosity with results in emulsion stability and especially in suspension stability) the product with the best results within the range being Bentone® SD-1.

Its use in our invention is aimed at increasing viscosity.

The amount used will depend on the viscosity (high, adequate or low) of the formulation according to the other coformulants chosen according to the invention.

It should be within the range of 0-20%, preferably 0-5%.

Bentonite has been described in suspensions of sulphonylureas, but with emulsifiers/dispersing agents other than those of this invention, and to modify viscosity in a completely different medium (different oil and coformulants).

Since the effect depends on the medium in which the viscosity modifier is used, it is not in the least evident or predictable that bentonite would have a beneficial effect in preventing the oil from separating in our formulation and moreover, to aid towards a good suspension and emulsion.

It is even less obvious that the use of bentonite is suitable in paraffin oils and with the expected effect.

Nevertheless, the main effect for the non-separation and stability of the Al is given by the organosilane derivative in the paraffin medium.

On the other hand, we have seen that a greater amount of Al does not necessarily imply that the amount of bentonite must be increased, in contrast to what a person skilled in the art may think. Moreover, we have verified that bentonite amounts of 2-5% are sufficient to maintain suitable viscosity for Al concentrations of 2-50%.

Greater amounts of Al (>50%) do not result in formulation properties—positive results in FAO tests—as good as those object of this invention (not more than 50% Al content, or preferably not more than 30%).

The best results for suspension and emulsion stability are found when the Al is <50%.

Our formulation necessarily contains nonionic surfactants (emulsifiers or dispersing agents)—these three concepts are used interchangeably.

Ionic emulsifiers may optionally and preferably be used, such as those described in emulsifier, dispersing agent or wetting agent catalogues for agriculture.

The ionic emulsifier is preferably of the salt of (mono-, di- or tri-) alkylbenzene sulphonate type, e.g. sodium (or calcium, or ammonium or ethanolamine) sulphonate and mixtures thereof.

A representative trade name for the ionic agent is Calsogen® 4814. The content in ionic agent is 0-20%, preferably 1-15%, and more preferably 5-10%.

Nonionic dispersing agents/emulsifiers must be present in an amount of 2-40%, depending on whether the ionic agent mentioned in the previous paragraph is used or not (if ionic agents are used, then the amount of nonionic dispersing agent is less). We differentiate between two groups of nonionic emulsifiers/dispersing agents (NIO-1 and NIO-2).

NIO-1 Group

Sulphonylureas contain a very small (but technically significant) percentage of crystallisation water.

When they are applied in the field, or even beforehand, if the medium they are formulated in favours the loss of said water, the sulphonylurea crystals have a great tendency to agglomerate, and this is another problem in the state of the art. Similarly, the milling process is industrially difficult using dispersing agents of the sulphosuccinate type (as described in patents regarding oil suspensions).

At least, we find great difficulty for the product, once ground, not to finish up as agglomerated crystals.

In order to solve this partial problem, part of the general problem of formulating sulphonylureas in oil, we have seen that the combination of two types of certain dispersing agents (NIO-1.A and NIO-1.B) have a surprising effect. This combination of special and surprising activity in sulphonylurea oil suspensions concerns two different types of polymers:

NIO-1.A: Dispersing agents the hydrophobic part of which is formed by poly-12-hydroxystearic acid (APHS/EO), and a hydrophilic part of which is formed by polyethylene oxide (the representative of which is the commercial product Atlox® 4914 or Hypermer B261 by Uniquema). Atlox 4912 is a nonionic A-B-A block copolymer dispersing agent of 12-hydroxystearic acid and polyethylene glycol.

Specifically, nonionic polymeric dispersing agents with an HLB of between 4-8, preferably 5-7.

Although the dispersing agents of the type mentioned are without a doubt the best, other similar types can be used, specifically those corresponding to the structures of commercial dispersing agents Hypermer A 109, A394, A409, 4914 or oligomeric Hypermer E475, E476, E488, all by Uniquema (ICI).

NIO-1.B: Dispersing agents of the condensed fatty acid type (the representative of which is commercial product Atlox® LP-1, or LP-5, or LP-6 by Uniquema).

These dispersing agents (preferably used in combination NIO-1.A:NIO-1.B of 5:1 to 1:5 and at a total concentration in the formulation of 0.1-10%, preferably between 0.1-2%) allow the milling process to be performed without obstructions in the ball mills, and the ground product to be stable for several days (a least 3 days) without any large crystals forming. This represents a logistic advantage, since the milling process (and the ground product) may be accomplished days before the final formulation.

In the tests, substitution of these dispersing agents (at 2%) for sulphosuccinates at the same concentration—and in the same isoparaffinic oil medium—shows that they are essential for good milling (obtaining and maintaining the desired crystal size).

NIO-2 Group

The use of emulsifiers in an amount of more than 10% is necessary for a good embodiment of this invention.

We have found that ethoxylated (and/or propoxylated) fatty acids (represented by Alkamul® VO/2003) have very good emulsifying properties when performing the final emulsion of the oil in water (which will be performed by the farmer).

Other typical emulsifiers used in agriculture can also be used (ethoxylated/propoxylated fatty alcohols, ethoxylated/propoxylated block copolymers, ethoxylated/propoxylated tristirilphenols, ethoxylated castor oil, etc.)

Please note that in order to obtain a good emulsion solves a partial problem of the invention—emulsifiers can be used that are not ethoxylated alcohols.

However, we have verified that biological activity is greater if ethoxylated fatty acids are used. It is also possible to combined several types of nonionic emulsifiers.

Preferable concentrations of nonionic emulsifiers are 5-20%, preferably 5-15%.

If no other emulsifier is used (that is not a dispersing agent) other than the ethoxylated acid fatty, the recommended proportions are of 2-25%, preferably 5-20%.

Suitable ratios of combinations of ionic and nonionic emulsifiers (e.g., Calsogen® 4814 and Alkamul VO/2003 NIO-2) are from 1:9 to 9:1, preferably 2:8 to 7:3.

Optionally, and in order to attend the requirements imposed by Guideline 91/414 in Appendix VI (i.e., FAO specifications regarding agrochemical formulations), it is convenient to use an antifoaming agent.

Any type of approved antifoaming agent for agrochemicals is suitable, whether it is a silane derivative or not, at a concentration of 0.05-5%, preferably from 0.5-1.5%.

The best antifoaming agent we have found for these formulations is of the type represented by the chemical structure of commercial product Amersil WS 930. There are no great differences with the use of other antifoaming agents.

Other coformulants may be added if required, this task is obvious for a person skilled in the art.

For example, an AI that is sensitive to light may be protected with UV blockers or absorbers; as well as additives to improve penetration (e.g., alkyl lactams, ethyl lactate, tnbutyl citrate), colorants, compounds that reduce phototoxicity ("safeners"), pH regulators e.g., acetic acid, citrus acid, buffers, antimicrobial agents, etc. (according to the special requirements of each AI).

We have observed that these types of coformulants do not have negative affects upon formulation properties, therefore any coformulant of this type, unless there are obvious chemical reasons not to use it (e.g., it hydrolyses sulphonylureas with total safety, causes undesirable precipitation), especially used below 5% (as a guideline), it must not be prevented by the formulation expert.

A coformulant that seems to be useful is the biuret, which has been observed to facilitate sulphonylurea stability, which has nothing to do with the incorporation of neat urea as claimed in several patents.

In order to facilitate comprehension of the invention and the use of chemical equivalents different to those specifically mentioned herein, we enclose as an integral part of the invention the product catalogues for use in agrochemical formulations of Exxon, Uniquema and Clariant that are current in June 2007 (or surviving companies), with which the person skilled in the art will not experience any problems in reproducing the invention, if necessary, with other dispersing agents, surfactants, emulsifiers, oils, etc.

Similarly, the oil suspension described in the present invention may be used to be combined with microcapsule formulations, specifically those described by the same inventors in the applications for European patents EP 6024299, EP 6006748 and PCT/EP07/002,809, and incorporated by reference to the combination of this invention with microcapsules.

The manner of incorporating microcapsules to the oil suspensions described herein is simple: Simply by mixing them in the desired concentration with gentle stirring in a reactor (anchor type stirrer).

If it were necessary to combine several phases, the use of emulsifiers is recommended; as explained in PCT/EP07/002,809.

Preferably the microcapsule formulation will have a continuous water phase and the necessary emulsifiers to emulsify the water phase in the oil (those typically used in agriculture).

If this is a reverse phase microcapsule formulation (e.g., micro-encapsulated glyphosate), the mixing is then more simple, it being highly recommended that both oil phases (the microcapsule formulation phase and that of the present invention) are miscible, or at least that they are miscible in the presence of suitable emulsifiers.

Example 1

We have tried to summarise some of the experiments in the long series of combinations we have tested in the following table, where we indicate the ingredients as well as the results both for the stability properties of the suspension, the emulsion performed by technical farmer, AI stability and biological activity.

Discussion of the results, and conclusions derived from said results have been mentioned above in the description.

The type of compound is indicated on each line.

The examples were performed with the preferred products named above, specifically paraffin oil Isopar® M, dispersing agents Calsogen CA (calcium phenylsulphonate, ionic emulsifier) Atlox® 4912 (derivative of 12-hydroxystearic acid, NIO-A.1 emulsifier), Silanos Break-Thru® S240 (organo-modified silane) Alkamul VO/2003 (ethoxylated fatty acid, NIO-A.2 emulsifier), Amersil® (antifoaming agent), Bentone® (viscosity modifier) in powder and Isopar® M (base oil).

One possible process (the most preferred) consists in mixing the ingredients except the viscosity modifier and grinding them altogether, dispersing the viscosity modifier at the end of the grinding process.

It is worth highlighting that for an adequate grinding process the presence of nonionic dispersing agents NIO-A.1 and NIO-A.2 is very highly recommended to avoid agglomeration of the crystals (we see that the combination of modified 12-hydrostearic acid dispersing agents, together with organomodified silanes is surprisingly effective to prevent primary agglomeration problems during grinding and also long-term).

Nevertheless, the Al (or Als) may be ground in the presence of the base oil (or a mixture of base oils) and dispersing agents and/or emulsifiers (e.g., Atlox® 4912' and Alkamul® VO/2003); and adding the remaining coformulants to the rest of the formulation after grinding.

The grinding should preferably produce crystals smaller than 5 µm. We have observed that the best stability is observed with crystals with a size of 1-3 µm, preferably when the mean is approximately 2 µm. This is easily achieved by using all the coformulants of the invention together, and almost impossible industrially (without increasing temperature and Al degradation) according to the state of the art processes.

We incorporate herein by reference the catalogues corresponding to products that may be used as coformulants according to our invention, by the companies Uniquema, Clariant (or companies inheriting said catalogued products) as well as application documents for patents EP 6024299, EP 6006748 and PCT/EP07/002,809, with special reference to the last document, that explains in detail how to incorporate a microcapsule suspension (either normal or reverse phase) to an oil suspension (in that case for microcapsules, here for sulphonylureas).

Active ingredient stability refers to the decomposition of the active ingredient in a test in an oven at 35° for 15 days with respect to the initial content of the freshly prepared formulation.

Biological activity refers to the herbicidal activity according to basic tests for each sulphonylurea.

Sorgum halepense seeds were used for herbicidal activity in comparison with Zea mays seeds, having performed the treatment when at least the 3 first leaves had formed.

In a greenhouse environment, 200 m² were used with each species, and they were treated with each product at its minimum recommended dose according to the e-Pesticide Manual of the BCPC e.g., In the case of nicosulfuron at 35 g/Ha—) with Table 1 showing the comparative results (in formulation stability: suspension without oil separation after 15 days +++; 0:2-0:5 mL ++; 0:5-1 mL as + and >1 mL as −; in emulsion stability the results are following 24 hours).

TABLE 1

| | A | B | C | D | E | F | G | H | I | J | K |
|---|---|---|---|---|---|---|---|---|---|---|---|
| Nicosulfuron | 4.82 | 21.90 | 4.80 | 4.80 | 4.80 | 21.90 | – | 4.82 | 4.82 | 21.90 | – |
| Tribenuron | – | – | – | – | – | – | 10.90 | – | – | – | – |
| Metsulfuron | – | – | – | – | – | – | 11.00 | – | – | – | 3.30 |
| Fluroxipir | – | – | – | – | – | – | – | – | – | – | 30.00 |
| Lambda-cyhalothrin | – | – | – | – | – | – | – | – | 10.00 | – | – |
| Tebuconazole | – | – | – | – | – | – | – | 10.00 | 5.00 | – | – |
| Ethoxylated hydroxystearic acid | 0.12 | 0.57 | 0.12 | 0.12 | 0.12 | 0.57 | 0.57 | 2.50 | 2.50 | 0.57 | 0.00 |
| Condensed fatty acid | 0.35 | 1.67 | 0.35 | 0.35 | 0.35 | 1.67 | 1.67 | 7.33 | 7.33 | 1.67 | 0.00 |
| Trisiloxane polyether | 19.58 | 14.20 | 19.58 | 19.58 | 19.58 | – | 14.20 | 10.00 | 10.00 | – | 19.00 |
| Dodecylbenzenesulphonate salt | 4.00 | 7.00 | 4.00 | 4.00 | 4.00 | 7.00 | 7.00 | 0.00 | 0.00 | 7.00 | 10.00 |
| Ethoxylated 18C fatty alcohol | 10.00 | 7.00 | 10.00 | 10.00 | 10.00 | 7.00 | 7.00 | 35.00 | 35.00 | 7.00 | 10.00 |
| Silicone anti-foaming agent | 0.38 | 0.38 | 0.38 | 0.38 | 0.38 | 0.38 | 0.38 | 0.05 | 0.05 | 0.38 | 0.00 |
| Bentonite in powder | 3.70 | 3.08 | 3.70 | 3.70 | 3.70 | 3.08 | 3.08 | 0.30 | 0.30 | 3.08 | 1.00 |
| Paraffin oil | 57.05 | 44.20 | 55.00 | 55.00 | 25.00 | – | 44.20 | 10.00 | 10.00 | 44.20 | 26.70 |
| Dioctyl sulphosuccinate | – | – | – | – | – | 12.13 | – | – | – | 14.20 | – |
| Solvesso 200 | – | – | – | – | – | 44.20 | – | 10.00 | 5.00 | – | – |
| Sunflower oil | – | – | – | – | 30.00 | – | – | 10.00 | 5.00 | – | – |
| Urea | – | – | – | 2.07 | 2.07 | 2.07 | – | – | – | – | – |
| Biuret | – | – | 2.07 | – | – | – | – | – | 5.00 | – | – |
| Formulation stability | +++ | +++ | +++ | +++ | + | – | +++ | ++ | + | – | ++ |

TABLE 1-continued

|                               | A    | B    | C    | D    | E    | F    | G       | H    | I    | J    | K    |
|-------------------------------|------|------|------|------|------|------|---------|------|------|------|------|
| Emulsion stability            | +++  | +++  | +++  | +++  | ++   | −    | +++     | ++   | +    | −    | +    |
| Al stability (% degraded)     | 2.8  | 1.7  | 1.4  | 1.6  | 2.0  | 4.9  | 3.4/2.9 | 1.3  | 0.7  | 4.9  | 3.4  |
| Herbicidal biological activity| 96   | 97   | 99   | 99   | 96   | 78   | 99      | 94   | 99   | 73   | 100  |

FIG. 1 shows the lack of phase separation in formulation B of Example 1 (GAT) versus phase separation in commercial formulation Motivell®, (nicosulfuron in oil suspension) marketed by BASF (Batch 161106-113 bought in Germany in June 2007) after 15 days standing and for 8 days at 54° C. This indicates a high percentage of the packages of this formulation, which is very representative of the state of the art, have phase separation before being used by the farmer, thus requiring strong stirring for its correct manipulation, as indicated on the label by "vor Gebrauch heftig schütteln" (stir well before use).

In order to perfectly understand the claims regarding the specified sulphonylureas, you must understand that the common name of one of them includes any herbicidal derivatives thereof, especially alkyl ethers or esters (usually "ethyl" or "methyl") and salts thereof. For example, when claiming tribenuron, the reader must understand that "tribenuron-methyl" is also being claimed. It is worth highlighting that in many documents sulphonylureas are referred to by their "incomplete" name (metsulfuron for metsulfuron-methyl).

The invention claimed is:

1. A stable agrochemical formulation in the form of an oil suspension, comprising (percentages by weight related to the total weight of the formulation):
    a) At least one herbicide at a concentration of 0.5-50%;
    b) At least one paraffin mineral oil at a concentration of 10-75%; and
    c) At least one organomodified silane compound at a concentration of 5-40% with coformulants until reaching 100% by weight of the formulation,
wherein said at least one herbicide is a sulphonylurea compound or derivative thereof, and wherein said at least one organomodified silane compound is a trisiloxane polyether.

2. The agrochemical formulation according to claim 1, wherein said at least one herbicide is amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, and active herbicidal derivatives and salts thereof.

3. The agrochemical formulation according to claim 1, further comprising at least one agrochemical active ingredient in addition to the sulphonylurea, said agrochemical being chosen from the group consisting of herbicides, insecticides, fungicides, plant hormones, semiochemicals and antibiotics.

4. The agrochemical formulation according to claim 2, wherein it combines:
    a) at least two sulphonylureas; or
    b) any sulphonylurea with one of the following agrochemicals: fluoroxypyr, diflufenican, lactofen, mesotrione, sulcotrione, fluorochloridone, metazachlor, clomazone (or a mixture of clomazone with metazachlor), pyrethroids, triazole fungicides, glyphosate, or gluphosinate.

5. The agrochemical formulation according to claim 1, wherein a nonionic dispersing agent chosen as one of the coformulants is an A-B-A block copolymer of 12-hydroxystearic acid and polyethylene glycol at a concentration of 0.1-10%.

6. The agrochemical formulation according to claim 1, wherein a nonionic dispersing agent chosen as one of the coformulants is of a condensed fatty acid at a concentration of 0.1-10%.

7. The agrochemical formulation according to claim 1, wherein said formulation has two nonionic dispersing agents, one a nonionic A-B-A block copolymer of 12-hydroxystearic acid with polyethylene glycol, and another dispersing agent being a condensed fatty acid, at a total concentration of both dispersing agents of 0.1-10%.

8. The agrochemical formulation according to claim 1, wherein one of the coformulants is chosen as an ionic emulsifier of an alkylbenzene sulphonate at a concentration of 2-15%.

9. The agrochemical formulation according to claim 1, wherein a nonionic emulsifier chosen as one of the coformulants is of an ethoxylated fatty acid at a concentration of 2-25%.

10. The agrochemical formulation according to claim 1, wherein a viscosity modifier chosen as one of the coformulants is of the bentonite group, at a concentration of 0.1-20%.

11. The agrochemical formulation according to claim 1, wherein said formulation contains:
    a) An active ingredient or a mixture of active ingredients at 0.5-50%;
    b) Paraffin mineral oil at 30-75%;
    c) Trisiloxane polyether at 5-40%;
    d) an A-B-A block copolymer of 12-hydroxystearic acid with polyethylene glycol at 0.1-10% as dispersing agent;
    e) a condensed fatty acid at 0.1-10% as dispersing agent;
    f) an ethoxylated fatty alcohol at 2-25%;
    g) an alkylbenzene sulphonate at 2-15%; and
    h) a bentonite at 0.1-20.

12. The agrochemical formulation according to claim 1, wherein said formulation contains a mixture of base oils formed by at least:
    i) 10% paraffin mineral oil;
    ii) 0-60% aromatic mineral oil;
    iii) 0-60% of vegetable oil;
    the concentration of i) and ii) not being able to be simultaneously 0%;
    and moreover where the total amount of base oils forms about 30-75%.

13. The agrochemical formulation according to claim 1, further comprising at least one micro-encapsulated agrochemical active ingredient.

14. A process for producing an agrochemical formulation in the form of an oil suspension according to claim 11 or claim 12, comprising the steps of
    i) Mixing the paraffin oil according to claim 11 b) or a combination of base oils according to claim 12 together with the active ingredient or ingredients according to claim 11 a) and with the dispersing agents referred to in claim 11 d) and e) as well as the organomodified silane of claim 11 c);

ii) Milling up to particle size <5 μm; and
iii) Adding the emulsifier according to claim 11 f) with stirring.

15. A method for controlling pests and/or agricultural diseases and/or increasing crop yield, comprising the step of applying a formulation according to claim 1 onto said crop.

16. The agrochemical formulation according to claim 1, wherein said at least one sulphonylurea is at a concentration of 2-30%.

17. The agrochemical formulation according to claim 1, wherein said at least one paraffin mineral is at a concentration of about 40-60%.

18. The agrochemical formulation according to claim 1, wherein said at least one organomodified silane compound is at a concentration of 10-25%.

19. The agrochemical formulation according to claim 2, wherein said active herbicidal derivative is a methyl, ethyl or alkyl ethers or esters, and salts thereof.

20. The agrochemical formulation according to claim 3, wherein said semiochemical is a confusion pheromone suitable for crop pests.

21. The agrochemical formulation according to claim 4, wherein said at least two sulphonylureas are metsulfuron with tribenuron, metsulfuron with thifensulfuron and nicosulfuron with rimsulfuron.

22. The agrochemical formulation according to claim 4, wherein said pyrethroid is alpha-cypermethrin, lambda-cyhalothrin, permethrin, resmethrin or allethrin.

23. The agrochemical formulation according to claim 4, wherein said triazole fungicide is tebuconazole, propiconazole or triadimenol.

24. The agrochemical formulation according to claim 4, wherein said glyphosate is in salt form or an acid.

25. The agrochemical formulation according to claim 4, wherein said gluphosinate is in salt form or an acid.

26. The agrochemical formulation according to claim 1, wherein said trisiloxane polyether is combined with sodium tetraborate.

27. The agrochemical formulation according to claim 1, wherein said sodium tetraborate is absolutely anhydrous.

28. The agrochemical formulation according to claim 5, wherein the concentration of said A-B-A block copolymer of 12-hydroxystearic acid and polyethylene glycol is 0.1-2%.

29. The agrochemical formulation according to claim 6, wherein said condensed fatty acid coformulant is at a concentration of 0.1-2%.

30. The agrochemical formulation according to claim 7, wherein said total concentration of both dispersing agents is 0.1-2%.

31. The agrochemical formulation according to claim 8, wherein said alkylbenzene sulphonate is calcium, sodium or ethanolamine.

32. The agrochemical formulation according to claim 8, wherein said alkylbenzene sulphonate is calcium dodecylbenzenesulphonate.

33. The agrochemical formulation according to claim 8, wherein said alkylbenzene sulphonate is at a concentration of 3-8%.

34. The agrochemical formulation according to claim 9, wherein said ethoxylated fatty acid coformulant is at a concentration of 5-20%.

35. The agrochemical formulation according to claim 10, wherein said bentonite group coformulant is at a concentration of 0.1-5%.

36. The agrochemical formulation according to claim 11, wherein said active ingredient or a mixture of active ingredients is at a concentration of 0.5-30%.

37. The agrochemical formulation according to claim 11, wherein said paraffin mineral oil is at a concentration of 40-60%.

38. The agrochemical formulation according to claim 11, wherein said trisiloxane polyether is at concentration of 10-25%.

39. The agrochemical formulation according to claim 11, wherein said A-B-A block copolymer is at a concentration of 0.1-2%.

40. The agrochemical formulation according to claim 11, wherein said condensed fatty acid is at a concentration of 0.1-2%.

41. The agrochemical formulation according to claim 11, wherein said ethoxylated fatty alcohol is at a concentration of 5-20%.

42. The agrochemical formulation according to claim 11, wherein said alkylbenzene sulphonate is calcium or sodium or ethanolamine dodecylbenzenesulphonate.

43. The agrochemical formulation according to claim 11, wherein said ionic emulsifier is at a concentration of 3-8%.

44. The agrochemical formulation according to claim 11, wherein said bentonite is at a concentration of 0.1-5%.

45. The agrochemical formulation according to claim 11, further comprising biuret at a concentration of 0.1-5%.

46. The agrochemical formulation according to claim 11, further comprising other coformulants to control pH, protect from light, antimicrobial agents, penetrants, phytotoxicity reducers, markers and colorants.

47. The agrochemical formulation according to claim 12, wherein said aromatic mineral oil is a naphtha mineral oil.

48. The agrochemical formulation according to claim 12, wherein said vegetable oil is linen, corn, coconut, rape, sunflower, or any other industrial vegetable oil.

49. The agrochemical formulation according to claim 12, wherein the total amount of base oils forms about 40-60%.

50. The process according to claim 14, wherein said particle size is <2 μm.

51. A method for preventing the agglomeration of crystals when grinding active ingredients in the presence of paraffin oil and trisiloxane polyether, comprising the step of adding to said ingredients a mixture of an A-B-A block copolymer of 12-hydroxystearic acid and polyethylene glycol and a condensed fatty acid; wherein said active ingredient is at least one sulphonylurea herbicide, said paraffin oil is at 30-75%, said trisiloxane polyether is at 5-40%, said A-B-A block copolymer is at 0.1-10% and said condensed fatty acid is at 0.1-10%.

* * * * *

UNITED STATES PATENT AND TRADEMARK OFFICE
CERTIFICATE OF CORRECTION

PATENT NO.       : 8,648,013 B2                                          Page 1 of 1
APPLICATION NO.  : 12/452168
DATED            : February 11, 2014
INVENTOR(S)      : Casaña Giner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 754 days.

Signed and Sealed this

Twenty-ninth Day of September, 2015

Michelle K. Lee
*Director of the United States Patent and Trademark Office*